United States Patent [19]

Gryaznov et al.

[11] 4,026,958

[45] May 31, 1977

[54] CATALYST FOR DEHYDROGENATION OR DEHYDROCYCLIZATION OF HYDROCARBONS

[76] Inventors: Vladimir Mikhailovich Gryaznov, Leninskie Gory MGU, korpus L. kv. II; Viktoria Petrovna Polyakova, ulitsa Trofimova 15, kv. 201; Evgeny Mikhailovich Savitsky, ulitsa Dm.Ulyanova D.N.R. 3, kv. 13; Evgenia Vladimirovna Khrapova, Nizhegorodskaya ulitsa, II"b", kv. 47, all of Moscow, U.S.S.R.

[22] Filed: Mar. 5, 1976

[21] Appl. No.: 664,412

Related U.S. Application Data

[60] Continuation of Ser. No. 179,585, Sept. 10, 1971, abandoned, which is a division of Ser. No. 874,080, Nov. 4, 1969, abandoned.

[52] U.S. Cl. .......................... 260/668 D; 260/673.5
[51] Int. Cl.$^2$ .......................................... C07C 5/18
[58] Field of Search ....... 260/668 D, 666 A, 669 R, 260/680 R, 683.3, 673.5

[56] References Cited

UNITED STATES PATENTS 3,562,346  2/1971  Smirnov et al. ................ 260/673.5

*Primary Examiner*—C. Davis

[57] ABSTRACT

A hydrocarbon such as cyclohexane is passed at a temperature of about 330°–575° C over a catalyst to effect dehydrogenation of the hydrocarbon, the catalyst being in the form of a membrane of an alloy of 90–98% palladium and 2–10% by weight of ruthenium.

4 Claims, No Drawings

CATALYST FOR DEHYDROGENATION OR DEHYDROCYCLIZATION OF HYDROCARBONS

CROSS RELATED APPLICATION

This application is a continuation of co-pending application Ser. No. 179,585 filed Sept. 10, 1971, and now abandoned, which in turn is a division of Ser. No. 874,080 filed Nov. 4, 1969 and now abandoned.

DETAILED DESCRIPTION

The present invention relates to catalysts for use in processes of dehydrogenation or dehydrocyclization of hydrocarbons accompanied by the evolution and absorption of hydrogen and, more particularly, to catalysts employed in the production of aromatic hydrocarbons or high-octane gasolines.

Catalysts for processes of dehydrogenation and dehydrocyclization of hydrocarbons are known which are based on palladium, for example, a catalyst containing 0.5 wt.% of palladium on a gumbrine carrier - an aluminosilicate containing 86.98 wt.% $SiO_2$, 4.14 wt.% $Al_2O_3$, 0.56 wt.% $Fe_2O_3$, 1.27 wt.% MgO, 1.33 wt.% CaO, and 0.41 wt.% $TiO_2$, having a specific surface of 260 $m^2/g$, said catalyst being employed in the process of dehydrogenation of cyclohexane. At a temperature of 470° C and under a pressure of 20 atm the yield of benzene is 40.2%.

Said catalyst cannot be formed into a membrane having selective permeability for hydrogen. This limits the yield of the main product and precludes the use of the catalyst for the simultaneous production of pure hydrogen.

It is an object of the present invention to provide a catalyst which gives a higher yield of final product and which can be formed into a membrane.

This object has been achieved by provision of a palladium-containing catalyst which according to the invention is a palladium-ruthenium alloy containing 90–98 wt.% of palladium and 2–10 wt.% of ruthenium.

Said catalyst is preferably an alloy consisting of 90 wt.% of palladium and 10 wt.% of ruthenium.

The catalyst of the present invention can be formed into tubes, films, foils and diaphragms of any shape.

The present catalyst makes it possible to increase the yield of the main product. Moreover, said catalyst can be used as a membrane having selective permeability for hydrogen. The hydrogen evolved in processes of dehydrogenation and dehydrocyclization diffuses through said catalyst, thus unbalancing the thermodynamic equilibrium of the process and increasing the yield of the main product.

The pure hydrogen evolved can be utilized in other processes where required. Employment of said catalyst in the form of a diaphragm dividing the reaction space prevents mixing of the initial and final reaction products and facilitates isolation and purification of the final product.

For a better understanding of the present invention, the following Examples are given by way of illustration.

EXAMPLE 1

In the process of the dehydrogenation of cyclohexane, a catalyst is used which is an alloy containing 98 wt.% palladium and 2 wt.% ruthenium. The catalyst is in the form of a foil 70 microns thick with a geometric surface of 100 $cm^2$. Before use in the process, the catalyst is treated at 350° C for 30 min with hydrogen which has been freed of oxygen and water vapor.

Dehydrogenation of cyclohexane is carried out in a quartz reactor in a stream of helium at 14 ml/min at a temperature of 350° C. Cyclohexane (Pure for analysis, $n_D^{20} = 1.4264$) in the amount of 0.1 microliter is passed over the catalyst after vaporization on packing. The reaction products are analyzed by chromatography using a column 1 m long with an inner diameter of 2 mm, filled with graphitized carbon black. When a flame-ionization detector is used, only benzene is detected in the reaction products.

The benzene yield is 49 wt.%.

EXAMPLE 2

Dehydrogenation of cyclohexane.

The process is carried out similarly to Example 1. Temperature 425° C. Composition of catalyst: pelladium 95 wt.%. ruthenium 5 wt.%. Benzene yield 72 wt.%.

EXAMPLE 3

Dehydrogenation of cyclohexane.

The process is carried out similarly to Example 1. Temperature 440° C. Composition of catalyst: palladium 95 wt.%, ruthenium 5 wt.%. Benzene yield 78 wt.%.

EXAMPLE 4

Dehydrogenation of cyclohexane.

The process is carried out similarly to Example 1. Temperature 330° C. Composition of catalyst: palladium 90 wt.%, ruthenium 10 wt.%. Benzene yield 88 wt.%.

EXAMPLE 5

Dehydrogenation of cyclohexane.

The process is carried out similarly to Example 1. Temperature 340° C. Composition of catalyst: palladium 90 wt.%, ruthenium 10 wt.%. Benzene yield 91 wt.%.

EXAMPLE 6

Dehydrocyclization of n-hexane.

The n-hexane ($n_D^{20} = 1.3751$) used in the example is free from benzene. The process is carried out similarly to Example 1. Temperature 465° C. Composition of catalyst; palladium 95 wt.%, ruthenium 5 wt.%. When a flame-ionization detector is used, only benzene is detected in the reaction products. Yield of benzene 28 wt.%.

EXAMPLE 7

Dehydrocyclization of n-hexane.

The process is carred out similarly to Example 1. Temperature 530° C. Composition of catalyst: palladium 95 wt.%, ruthenium 5 wt.%. Benzene yield 50 wt.%.

EXAMPLE 8

Dehydrocyclization of n-hexane.

The process is carried out similarly to Example 1. Temperature 575° C. Composition of catalyst: palladium 95 wt.%, ruthenium 5 wt.%. Benzene yield 58 wt.%.

What is claimed is:

1. A process for the dehydrogenation of cyclohexane to benzene which comprises passing the cyclohexane in vapor form at a temperature of about 330° C to about 575° C over a catalyst comprising a membrane of an alloy consisting of 90 to 98% by weight of palladium and 2 to 10% by weight of ruthenium.

2. A process as claimed in claim 1 wherein the catalyst membrane is formed with a thickness of about 70 microns.

3. A process as claimed in claim 1 wherein the alloy consists of 90% palladium and 10% ruthenium.

4. A process as claimed in claim 1 wherein the temperature is about 330° to 340° C., and the alloy consists of 90% palladium and 10% ruthenium.

* * * * *